United States Patent
Wu et al.

(10) Patent No.: US 6,509,289 B1
(45) Date of Patent: Jan. 21, 2003

(54) HYDRODEALKYLATION PROCESS AND CATALYST COMPOSITION

(75) Inventors: An-hsiang Wu, Bartlesville, OK (US); Charles A. Drake, Nowata, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/488,273

(22) Filed: Jan. 20, 2000

Related U.S. Application Data

(62) Division of application No. 09/022,486, filed on Feb. 12, 1998, now Pat. No. 6,037,302, which is a division of application No. 08/764,366, filed on Dec. 12, 1996, now Pat. No. 5,763,721.

(51) Int. Cl.[7] .................... B01J 27/14; B01J 21/02; B01J 21/08; B01J 27/19

(52) U.S. Cl. ............ 502/208; 502/204; 502/207; 502/210; 502/211; 502/213; 502/214; 502/206; 502/240; 502/254; 502/258; 502/219; 502/220; 502/221; 502/222; 502/223

(58) Field of Search ............... 502/208, 210, 502/211, 213, 214, 240, 254, 258, 204, 206, 207, 219–223

(56) References Cited

U.S. PATENT DOCUMENTS

| | | | | |
|---|---|---|---|---|
| 2,799,661 A | | 7/1957 | DeRosset | 252/465 |
| 2,960,545 A | | 11/1960 | Seubold | 585/487 |
| 3,617,528 A | | 11/1971 | Hilfman | 208/216 |
| 3,629,146 A | | 12/1971 | Adams | 252/435 |
| 3,761,516 A | | 9/1973 | Khoobiar | 260/530 N |
| 3,980,586 A | | 9/1976 | Mitchell | 252/455 R |
| 3,992,468 A | | 11/1976 | Cosyn et al. | 260/672 R |
| 4,038,337 A | | 7/1977 | Manara et al. | 260/683.2 |
| 4,080,284 A | | 3/1978 | Mitchell | 208/111 |
| 4,456,699 A | | 6/1984 | Hensley, Jr. et al. | 502/208 |
| 4,483,767 A | | 11/1984 | Antos et al. | 208/138 |
| 4,513,097 A | | 4/1985 | Angmorter et al. | 502/211 |
| 4,677,240 A | | 6/1987 | Carlson et al. | 585/488 |
| 4,687,568 A | | 8/1987 | Kukes et al. | 208/251 H |
| 4,689,314 A | | 8/1987 | Martinez et al. | 502/210 |
| 4,708,945 A | | 11/1987 | Murrell et al. | 502/263 |
| 4,778,779 A | | 10/1988 | Murrell et al. | 502/263 |
| 4,786,404 A | | 11/1988 | Kemp | 208/217 |
| 4,818,743 A | | 4/1989 | Simpson et al. | 502/211 |
| 4,831,007 A | | 5/1989 | Murrell et al. | 502/254 |
| 4,891,127 A | | 1/1990 | Murrell et al. | 208/111 |
| 5,139,989 A | | 8/1992 | Chou et al. | 502/214 |
| 5,453,411 A | | 9/1995 | Dai et al. | 502/315 |
| 5,536,687 A | | 7/1996 | Ward | 502/67 |
| 5,714,660 A | * | 2/1998 | Wu et al. | 585/488 |
| 5,763,721 A | * | 6/1998 | Wu et al. | 585/489 |
| 5,856,609 A | * | 1/1999 | Wu et al. | 585/489 |
| 6,037,302 A | * | 3/2000 | Wu et al. | 502/208 |

* cited by examiner

*Primary Examiner*—Mark L. Bell
*Assistant Examiner*—Patricia L. Hailey
(74) *Attorney, Agent, or Firm*—McDermott, Will & Emery

(57) ABSTRACT

A catalyst composition and a process for hydrodealkylating a $C_9+$ aromatic compound such as, for example, 1,2,4-trimethylbenzene to a $C_6$ to $C_8$ aromatic hydrocarbon such as a xylene are disclosed. The composition comprises an alumina, a metal oxide, a phosphorus oxide and optionally, an acid site modifier selected from the group consisting of silicon oxides, sulfur oxides, boron oxides, magnesium oxides, tin oxides, titanium oxides, zirconium oxides, molybdenum oxides, germanium oxides, indium oxides, lanthanum oxides, cesium oxides, and combinations of any two or more thereof. The process comprises contacting a fluid which comprises a $C_9+$ aromatic compound with the catalyst composition under a condition sufficient to effect the conversion of a $C_9+$ aromatic compound to a $C_6$ to $C_8$ aromatic hydrocarbon.

20 Claims, No Drawings

HYDRODEALKYLATION PROCESS AND CATALYST COMPOSITION

This application is a divisional of application Ser. No. 09/022,486, filed Feb. 12, 1998, now U.S. Pat. No. 6,037, 302, which is a divional of application Ser. No. 08/764,366, filed Dec. 12, 1996, now U.S. Pat. No. 5,763,721.

FIELD OF THE INVENTION

This invention relates to a catalyst composition useful for converting a $C_9+$ aromatic compound to a $C_6$ to $C_8$ aromatic hydrocarbon, a process for producing the composition, and a process for using the composition in a hydrodealkylation process.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the aromatization of gasoline to aromatic hydrocarbons by catalytic cracking in the presence of a catalyst. The aromatic hydrocarbons produced by the aromatization process include $C_6$ to $C_8$ hydrocarbons such as benzene, toluene and xylenes (hereinafter collectively referred to as BTX) which can be useful feedstocks for producing various organic compounds and polymers. However, heavier, less useful aromatic compounds are also produced during the aromatization process. It is, therefore, highly desirable to convert these compounds to the more useful BTX.

Though a metal oxide-promoted alumina such as $Cr/Al_2O_3$ has been used as catalyst in a hydrodealkylation process, the conversion of a $C_9+$ aromatic compound and the selectivity to BTX are generally not as high as one skilled in the art would desire. It is also well known to one skilled in the art that alumina is an acidic metal oxide containing acid sites. One of the possible reasons for such low conversion and low selectivity is probably due to the acidity of an alumina-based catalyst.

However, a catalyst used in the hydrodealkylation of these heavier aromatic compounds is generally deactivated in a rather short period because of depositions of carbonaceous material such as, for example, coke on the surface of the catalyst. Generally, the more active the catalyst is, the more rapid deposition of coke on the catalyst is observed.

Accordingly, there is an ever-increasing need to develop a catalyst and a process for converting these heavier and less useful aromatic compounds to the more valuable BTX hydrocarbons (hereinafter referred to as hydrodealkylation process) and, in the meantime, for suppressing the coke formation. Such development would also be a significant contribution to the art and to the economy.

SUMMARY OF THE INVENTION

An object of this invention is to provide a catalyst composition which can be used to convert a $C_9+$ aromatic compound to a $C_6$ to $C_8$ aromatic hydrocarbon. Also an object of this invention is to provide a process for producing the catalyst composition. Another object of this invention is to provide a process which can employ the catalyst composition to convert $C_9+$ aromatic compounds to $C_6$ to $C_8$ aromatic compounds. An advantage of the catalyst composition is that it suppresses coke deposits thereon and exhibits high hydrodealkylation activity, satisfactory yield of xylenes and BTX, and good stability. Other objects and advantages will becomes more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition is a metal oxide-promoted alumina having incorporated therein an acid site modifier wherein the metal of the metal oxide is selected from the group consisting of chromium, cobalt, molybdenum, nickel, rhodium, palladium, platinum, tungsten, and combinations of any two or more thereof.

According to a second embodiment of the invention, a process for producing a composition which can be used as catalyst in a hydrodealkylation process is provided. The process comprises, consists essentially of, or consists of (1) contacting an alumina, which can be optionally calcined before being contacted, with an acid site modifier precursor under a condition sufficient to incorporate the acid site modifier into the alumina to form an acid site-modified alumina wherein the precursor is selected from the group consisting of silicon-containing compounds, sulfur-containing compounds, boron containing compounds, magnesium-containing compounds, tin-containing compounds, titanium-containing compounds, zirconium-containing compounds, germanium-containing compounds, indium-containing compounds, lanthanum-containing compounds, cesium-containing compounds, and combinations of any two or more thereof; (2) contacting the acid site-modified alumina with a phosphorus-containing compound, contemporaneously with a metal compound whose metal is selected from the group consisting of chromium, cobalt, molybdenum, nickel, rhodium, palladium, platinum, tungsten, and combinations of any two or more thereof whereby a modified alumina is formed; and (3) either calcining the modified alumina or contacting the modified alumina with steam under a condition sufficient to effect the conversion of the metal compound to its corresponding metal oxide wherein the acid site modifier precursor, phosphorus-containing compound, and the metal compound are each present in an amount that is sufficient to convert each of them to corresponding oxide form. The process can also comprise, consist essentially of, or consist of, (1) contacting an alumina with both a phosphorus-containing compound and a metal compound, simultaneously, under a condition sufficient to incorporate the metal compound into the metal alumina to form a modified alumina wherein the alumina can be optionally calcined before being contacted; and the metal of the metal compound is selected from the group consisting of chromium, cobalt, molybdenum, nickel, rhodium, palladium, platinum, tungsten, and combinations of any two or more thereof; and (2) contacting the modified alumina with steam under a condition sufficient to effect the conversion of the metal compound to its corresponding metal oxide wherein the amount of the metal compound or phosphorus-containing compound is the amount that is sufficient to convert the metal compound or phosphorus compound to its oxide form.

According to a third embodiment of the present invention, a process which can be used for converting a $C_9+$ aromatic compound to a $C_6$ to $C_8$ aromatic compound is provided which comprises, consists essentially of, or consists of, contacting a fluid which comprises a $C_9+$ aromatic compound, optionally in the presence of an inert fluid such as a hydrogen-containing fluid, with a catalyst composition which is the same as disclosed above in the first embodiment of the invention under a condition effective to convert a $C_9+$ aromatic compound to an aromatic hydrocarbon containing 6 to 8 carbon atoms per molecule.

According to a fourth embodiment of the invention a process which can be used for improving the yield of BTX or xylenes, or both, in a hydrodealkylation of a $C_9+$ aromatic compound is provided. The process comprises, consists essentially of, or consists of contacting an alumina-containing catalyst composition with a steam. The catalyst composition can be the same as that disclosed in the first embodiment of the invention.

DETAILED DESCRIPTION OF THE INVENTION

According to the first embodiment of the invention, a composition which can be used as catalyst in a hydrodealkylation process for converting a $C_9+$ aromatic compound to a $C_6$ to $C_8$ aromatic hydrocarbon is provided. The composition can comprise, consist essentially of, or consist of, a metal oxide-promoted alumina having incorporated therein, or impregnated thereon, an acid site modifier selected from the group consisting of silicon oxides, phosphorus oxides, sulfur oxides, boron oxides, magnesium oxides, tin oxides, titanium oxides, zirconium oxides, molybdenum oxides, germanium oxides, indium oxides, lanthanum oxides, cesium oxides, and combinations of any two or more thereof wherein the acid site modifier is present in the composition in a BTX selectivity-improving amount to improve the selectivity to BTX when the composition is used in a hydrodealkylation process.

According to the first embodiment of the invention, the weight ratio of the acid site modifier to the metal oxide-promoted alumina can be any ratio so long as the ratio can suppress or reduce the formation or deposition of coke on an alumina catalyst during the hydrodealkylation process for converting of a $C_9+$ aromatic compound to a $C_6$ to $C_8$ aromatic hydrocarbon. Generally, the ratio can be in the range of from about 0.000:1 to about 1:1, preferably about 0.001:1 to about 1:1, and most preferably 0.005:1 to 0.5:1. However, if the acid site modifier is a silicon oxide, the ratio can be in the range of from about 0.0001:1 to about 0.14:1, preferably about 0.0005:1 to about 0.14:1, more preferably about 0.001:1 to about 0.12:1 and most preferably from 0.005:1 to 0.11:1 for an effective dehydroalkylation conversion and coke reduction or suppression. Alternatively, a silicon oxide can be present in the catalyst composition in the range of from about 0.01 to about 12.5, preferably about 0.05 to about 12.5, more preferably about 0.1 to about 11, and most preferably 0.5 to 10 grams per 100 grams of the catalyst composition. The weight ratio of a phosphorus oxide to a metal oxide-promoted alumina can be the same as the ratio of an acid site modifier to a metal oxide-promoted alumina as disclosed above.

Any metal oxide-promoted alumina which is known to one skilled in the art to be capable of catalyzing a hydrodealkylation of a $C_9+$ aromatic compound to a $C_6$ to $C_8$ aromatic hydrocarbon can be employed in the present invention. The alumina can be α-alumina, β-alumina, γ-alumina, η-alumina, δ-alumina, or combinations of any two or more thereof. The presently preferred alumina is a γ-alumina having a surface area in the range of from about 40 to about 300 $m^2/g$, a total pore volume in the range of from about 0.1 to about 1.

Any metal oxide that, when incorporated into an alumina, is capable of promoting the hydrodealkylation of a $C_9+$ aromatic compound to a $C_6$ to $C_8$ aromatic hydrocarbon can be employed in the invention. Presently, it is preferred that the metal oxide is selected from the group consisting of molybdenum oxides, chromium oxides, cobalt oxides, nickel oxide, rhodium oxides, palladium oxides, platinum oxides, tungsten oxides, and combinations of any two or more thereof wherein the oxidation state of the metal can be any available oxidation state. For example, in the case of a molybdenum oxide, the oxidation state of molybdenum can be 2, 3, 4, 5, 6, or combinations of any two or more thereof. The presently preferred metal oxide-promoted alumina is a $Mo/Al_2O_3$ wherein the $Mo/Al_2O_3$ denotes an alumina promoted with a molybdenum oxide. The presently more preferred metal oxide is a molybdenum(VI) oxide. These metal oxide-promoted aluminas are commercially available. However, it is preferred they be produced by the process disclosed in the second embodiment of the invention. The weight percent (%) of a metal oxide to the catalyst composition can be any weight % so long as such weight % can be effective on a hydrodealkylation process. The weight % can be in the range of from about 0.1% to about 60%, preferably about 0.5 to about 50%, and most preferably 1 to 40%. If a combination of metal oxides is employed, the molar ratio of the second metal oxide, or the third metal oxide, or the fourth metal oxide to the first metal oxide can be in the range of about 0.01:1 to about 100:1.

According to the present invention, any acid site modifier that, as compared to use of a metal oxide-promoted alumina only, can effect the reduction of coke deposition on the metal oxide-promoted alumina, or the increase in the yield of BTX or xylenes, or both, during the conversion of a $C_9+$ aromatic compound to a $C_6$ to $C_8$ aromatic hydrocarbon can be employed. Presently it is preferred that the acid site modifier is selected from the group consisting of sulfur oxides, silicon oxides, phosphorus oxides, boron oxides magnesium oxides, tin oxides, titanium oxides, zirconium oxides, molybdenum oxides, germanium oxides, indium oxides, lanthanum oxides, cesium oxides, and combinations of any two or more thereof.

Any methods known to one skilled in the art for incorporating a compound or a portion thereof into an alumina such as, for example, impregnation or extrusion can be employed for producing the composition of the present invention. However, it is presently preferred the composition be produced by the process disclosed in the second embodiment of the invention.

As disclosed above, the alumina can be α-alumina, β-alumina, γ-alumina, η-alumina, δ-alumina, or combinations of any two or more thereof. The presently preferred alumina is γ-alumina having a surface area in the range of from about 40 to about 300 $m^2/g$, a total pore volume in the range of from about 0.1 to about 1. These aluminas are commercially available.

An alumina is generally first treated with an acid site modifier precursor. According to the second embodiment of the present invention, any acid site modifier precursor which can be converted to a acid site modifier, as disclosed in the first embodiment of the invention, that, as compared to use of a metal oxide-promoted alumina only, can effect the improvement of selectivity to BTX or xylene or the reduction of coke in a hydrodealkylation process can be employed. Presently it is preferred that a acid site modifier precursor be selected from the group consisting of sulfur-containing compounds, boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof.

Generally any silicon-containing compounds which can be converted to a silicon oxide that are effective to enhance hydrodealkylation of a $C_9+$ aromatic compound when used with a metal oxide-promoted alumina can be used in the present invention. Examples of suitable silicon-containing compounds can have a formula of $(R)(R)(R)Si-(-O_mSi(R)(R))_nR$ wherein each R can be the same or different and is independently selected from the group consisting of alkyl radicals, alkenyl radicals, aryl radicals, alkaryl radicals, aralkyl radicals, and combinations of any two or more thereof; m is 0 or 1; and n is 1 to about 10 wherein each radical can contain 1 to about 15, preferably 1 to about 10 carbon atoms per radical. Specific examples of such polymers include, but are not limited to, silicon-containing polymers such as poly(phenylmethylsiloxane), poly(phenylethylsiloxane), poly(phenylpropylsiloxane), hexamethyldisiloxane, decamethyltetrasiloxane, diphenyltetramethyldisiloxane, and combinations of any two or more thereof. Other silicon-containing compounds include organosilicates such as, for example, tetraethyl orthosilicate, tetrabutyl orthosilicate, tetrapropyl orthosilicate, or combination of any two or more thereof. A number of well known silylating agents such as trimethylchlorosilane, chloromethyldimethylchlorosilane, N-trimethylsilylimidazole, N,O-bis(trimethylsilyl) acetamide, N-methyl-N-trimethylsilyltrifluoroacetamide, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl)aminopropyl]trimethoxysilane, cyanoethyltrimethoxysilane, aminopropyltriethoxysilane, phenyltrimethoxysilane, (3-chloropropyl)trimethoxysilane, (3-mercaptopropyl)trimethoxysilane (3-glycidoxypropyl)trimethoxysilane, vinyltris(β-methoxyethoxy)silane, (γ-methacryloxypropyl)trimethoxysilane, vinylbenzyl cationic silane, (4-aminopropyl)triethoxysilane, [γ-(β-aminoethylamino)propyl]trimethoxysilane, (γ-glycidoxypropyl)trimethoxysilane, [β-(3,4-epoxycyclohexyl)ethyl]trimethoxysilane, (β-mercaptoethyl)trimethoxysilane, (γ-chloropropyl)trimethoxysilane, and combinations of any two or more thereof can also be employed. The presently preferred silicon-containing compounds are tetraethyl orthosilicate and poly(phenylmethyl) siloxane.

According to the present invention, any sulfur-containing compound that can be converted to a sulfur oxide upon calcining can be employed in the present invention. Example of suitable sulfur containing compounds include, but are not limited to, $(RSH)_n$, $RS_nR$, $RS(O)R$, $RS(O)(O)R$, $M_zS$, $SX_z$, $SO_zX_z$, $CO_mS_z$, $M_zH_mSO_4$, or combinations of any two or more thereof wherein each R, m, and n are the same as those disclosed above, z is a number that fills the proper valency of M, O, or X in which M is an alkali metal ion, an alkaline earth metal ion, an ammonium ion, or H, and X is a halogen or hydrogen. Specific examples of sulfur-containing compounds include, but are not limited to, ammonium sulfide, sodium sulfide, ammonium hydrogen sulfate, sodium hydrogen sulfide, potassium hydrogen sulfide, dimethyl disulfide, methyl mercaptan, diethyl disulfide, dibutyl trisulfide, sulfuryl chloride, sulfur monochloride, dinonyl tetrasulfide, hydrogen sulfide, carbon disulfide, carbonyl sulfide, sulfonyl chloride, or combinations of any two or more thereof.

According to the present invention, any boron-containing compound which, upon being incorporated into a metal oxide-promoted alumina can be converted into a boron oxide can be used in the present invention. Examples of suitable boron-containing compounds include, but are not limited to boric acid, borane-ammonium complex, boron trichloride, boron phosphate, boron nitride, triethyl borane, trimethyl borane, tripropyl borane, trimethyl borate, triethyl borate, tripropyl borate, trimethyl boroxine, triethyl boroxine, tripropyl boroxine, and combinations of any two or more thereof.

Examples of suitable magnesium-containing compounds include, but are not limited to, magnesium formate, magnesium acetate, magnesium bromide, magnesium bromide diethyl etherate, magnesium chloride, magnesium fluoride, magnesium nitrate, magnesium sulfate, dibutyl magnesium, magnesium methoxide, and combinations of any two or more thereof.

Similarly, examples of suitable tin-containing compound include, but are not limited to, stannous acetate, stannic acetate, stannous bromide, stannic bromide, stannous chloride, stannic chloride, stannous oxalate, stannous sulfate, stannic sulfate, stannous sulfide, and combinations of any two or more thereof.

Examples of suitable titanium-containing compounds include, but are not limited to, titanium zinc titanate, lanthanum titanate, titanium tetramides, titanium tetramercaptides, titanium tetrabutoxide, titanium tetramethoxide, titanium tetraethoxide, titanium tetrapropoxide, titanium tetrachloride, titanium trichloride, titanium bromide, and combinations of any two or more thereof.

Similarly, examples of suitable zirconium-containing compounds include, but are not limited to, zirconium acetate, zirconium formate, zirconium chloride, zirconium bromide, zirconium butoxide, zirconium tert-butoxide, zirconium citrate, zirconium ethoxide, zirconium methoxide, zirconium propoxide, and combinations of any two or more thereof.

Examples of suitable germanium-containing compounds include, but are not limited to, germanium chloride, germanium bromide, germanium ethoxide, germanium fluoride, germanium iodide, germanium methoxide, and combinations of any two or more thereof. Examples of suitable indium-containing compounds include, but are not limited to indium acetate, indium bromide, indium chloride, indium fluoride, indium iodide, indium nitrate, indium phosphide, indium selenide, indium sulfate, and combinations of any two or more thereof. Examples of suitable lanthanum-containing compounds include, but are not limited to, lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, lanthanum titanate, and combinations of any two or more thereof.

An alumina can be optionally calcined before it is used in the second embodiment of the invention to remove any possible contamination(s) in the alumina. The condition for calcining an alumina can be any condition known to one skilled in the art. The calcining can also be carried out under the condition disclosed hereinbelow.

Generally, in the first step of the process of the second embodiment of the invention, an alumina can be combined with an acid site modifier precursor in any suitable weight ratios which would result in the weight ratios of a acid site modifier to a metal oxide-promoted alumina disclosed in the first embodiment of the invention. Presently it is preferred that such combination be carried out in a suitable liquid to form an incipient wetness alumina-precursor mixture. The combining of an alumina and an acid site modifier can be carried out at any temperature. Generally, the temperature can be in the range of from about 15° C. to about 100° C., preferably about 20+ C. to about 100° C., and most preferably 20° C. to 60° C. under any pressure, preferably atmospheric pressure, for any length so long as the acid site modifier and the alumina are well mixed, generally about 1 minute to about 15 hours, preferably about 1 minute to about 5 hours.

Upon completion of incorporating the acid site modifier precursor into an alumina, an acid site-modified alumina is formed. In the next step of the process, the acid site-modified aluminum is then contacted, generally mixed, with a metal compound which can be converted, in the next step of the process, to a metal oxide shown in the first embodiment of the invention. In this step, a modified alumina is produced. The contacting can be carried out by the same procedure as disclosed in the first step of the second embodiment of the invention. The metal of a suitable metal compound is selected from the group consisting of chromium, cobalt, molybdenum, nickel, rhodium, palladium, platinum, tungsten, and combinations of any two or more thereof.

The presently preferred process for incorporating a phosphorus-containing compound and a metal oxide into an alumina is that the incorporation of the phosphorus-containing compound into the alumina is carried out simultaneously, or contemporaneously with, the incorporation of the metal compound to form a modified alumina. More specifically, a phosphorus-containing compound and a metal compound are simultaneously contacted with, or co-impregnated onto, an alumina. The condition for carrying out this simultaneous contacting of both a phosphorus-containing compounds and a metal compound can be the same as that disclosed above in the first step of the second embodiment of the invention.

Any phosphorus-containing compounds that, when impregnated onto or incorporated into a metal oxide-promoted alumina can be converted into a phosphorus oxide and are capable of reducing coke deposition on a metal oxide-promoted alumina, as compared to the use of the metal oxide promoted alumina only, can be used in the present invention. Examples of suitable phosphorus-containing compounds include, but are not limited to, phosphorus pentoxide, phosphorus oxychloride, phosphoric acid, phosphines having the formula of $P(OR)_3$, $P(O)(OR)_3$, $P(O)(R)(R)(R)$, $P(R)(R)(R)$, and combinations of any two or more thereof wherein R is the same as that disclosed above.

Examples of suitable metal compounds include, but are not limited to, molybdenum(II) acetate, ammonium molybdate, ammonium dimolybdate, ammonium heptamolybdate, ammonium phosphomolybdate molybdenum(III) bromide, molybdenum(II) chloride, molybdenum chloride, molybdenum(V) chloride, molybdenum hexacarbonyl, molybdenum(IV) sulfide, sodium molybdate, potassium molybdate, molybdenum oxychloride, molybdenum fluoride, molybdenum(VI) tetrachloride oxide, ammonium tetrathiomolybdate, chromium (II) acetate, chromium(III) acetate, chromium(III) acetylacetonate, chromium(II) chloride, chromium(III) chloride, chromium(II) fluoride, chromium(III) fluoride, chromium hexacarbonyl, chromium(III) nitrate, chromium nitride, chromium(III) 2,4-pentanedionate, chromium(III) perchlorate, chromium(III) potassium sulfate, chromium (III) sulfate, chromium(III) telluride, cobalt(II) acetate, cobalt(II) acetylacetonate, cobalt(III) acetylacetonate, cobalt (II) benzoylacetonate, cobalt(II) bromide, cobalt(II) carbonate, cobalt(II) chloride, cobalt(II) 2-ethylhexanoate, cobalt(II) fluoride, cobalt(III) fluoride, cobalt(II) iodide, cobalt(II) iodide, cobalt(II) 2,3-naphthalocyanine, cobalt(II) nitrate, cobalt(II) oxalate, cobalt(II) perchlorate, cobalt(II) phthalocyanine, cobalt(II) sulfate, cobalt(II) thiocyanate, cobalt(II) tungstate, nickel(II) acetate, nickel(II) acetylacetonate, nickel(II) bromide, nickel(II) carbonate, nickel(II) chloride, nickel(II) nitrate, nickel(II) perchlorate, nickel phosphide, nickel(II) sulfate, nickel sulfide, nickel(II) titanate, palladium(II) acetate, palladium(II) acetylacetonate, palladium(II) bromide, palladium(II) iodide, palladium(II) nitrate, palladium(II) sulfate, palladium(II) sulfide, rhodium(II) acetate rhodium(III) acetylacetonate, rhodium(III) bromide, rhodium(III) chloride, rhodium(III) nitrate, rhodium(II) octanoate, rhodium(III) phosphate, rhodium(III) sulfate, tungsten(V) bromide, tungsten(IV) chloride, tungsten(VI) chloride, tungsten hexacarbonyl, tungsten(VI) oxychloride, tungsten(IV) sulfide, tungstic acid, and combinations of any two or more thereof. The presently preferred metal compounds include, but are not limited to, molybdenum(II) acetate, ammonium molybdate, ammonium dimolybdate, ammonium heptamolybdate, ammonium tetrathiomolybdate, phosphomolybdate, molybdenum(III) bromide, molybdenum(II) chloride, molybdenum(IV) chloride, molybdenum(V) chloride, molybdenum hexacarbonyl, molybdenum(IV) sulfide, sodium molybdate, potassium molybdate, molybdenum oxychloride, molybdenum fluoride, molybdenum(VI) tetrachloride oxide, and combinations of any two or more thereof. The presently most preferred metal compound is ammonium heptamolybdate for it is readily available and effective.

In the next step, the modified alumina is subject to calcination under a condition that can include a temperature in the range of from about 300° C. to about 1000° C., preferably about 350° C. to about 750° C., and most preferably 400° C. to 650° C. under a pressure in the range of from about 1 to about 10, preferably about 1 atmospheres for a period in the range of from about 1 to about 30, preferably about 1 to about 20, and most preferably 1 to 15 hours.

Preferably the modified alumina is treated with a steam under a suitable condition sufficient to effect the conversion of the acid site-modifier precursor and the metal compound, which have been incorporated into the alumina, to their corresponding oxide form. The modified alumina can be air dried to remove most moisture content before being steam-treated. Air drying can be carried out at a temperature for about 25° C. to about 150° C. for about 1 minute to about 30 hours under any pressure such as atmospheric pressure. The air-dried modified alumina can then be treated with a steam. Generally the steam temperature can be in the range of from about 120° C. to about 1500° C., preferably about 200° C. to about 1200° C., and most preferably 250° C. to 1000° C. The treatment period can be as short as 5 minutes to as long as about 30 hours so long as it is sufficient to convert the acid site modifier precursor and metal compound to their oxide form. The treatment can be carried out under a pressure in the range of from about atmospheric pressure to about 2,000, preferably to about 1,500, and most preferably to 1000 psig.

The process disclosed above can also be carried out without the practice of the first step of the process.

The composition of the invention then can be, if desired, pretreated with a reducing agent before being used in a hydrodealkylation process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250+ C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process useful for converting a $C_9+$ aromatic compound to a $C_6$ to $C_8$ aromatic hydrocarbon comprises, consists essentially of, or consists of contacting a fluid stream comprising a $C_9+$ aromatic compound and, optionally, in the presence of an inert fluid such as, for example, hydrogen-containing fluid, with a catalyst composition under a condition sufficient to effect the conversion of a $C_9+$ aromatic compound to a $C_6$ to $C_8$ aromatic hydrocarbon. The inert fluid can be hydrogen, nitrogen, helium, argon, carbon dioxide, neon, steam, and combinations of any two or more thereof. The presently preferred inert fluid is a hydrogen-containing fluid. The inert fluid can also be fed separately into contact with a $C_9+$ aromatic compound and a catalyst. The catalyst composition is the same as that disclosed in the first embodiment of the invention.

The term "fluid" is used herein to denote gas, liquid, vapor, or combinations of two or more thereof. The term "$C_9+$ aromatic compound" is referred to, unless otherwise indicated, as a substituted aromatic compound containing at least 9 carbon atoms per molecule. Preferably the substituted aromatic compound has the formula of $R'_q Ar$ wherein each R' is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is a phenyl group. More preferably R' is an alkyl radical having 1 to about 10 carbon atoms and the aromatic compound has 9 to about 16 carbon atoms per molecule. Most preferably the aromatic compound contains 9 to 12 carbon atoms per molecule.

Any fluid which contains a $C_9+$ aromatic compound as disclosed above can be used as the feed for the process of this invention. The origin of this fluid feed is not critical. However, a preferred fluid feed is a $C_9+$ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, 1,3-diethylbenzene, and the like can also be present in the fluid. Benzene, toluene, ethylbenzene and xylenes are generally substantially absent from the fluid, i.e., the amount of each of these aromatic hydrocarbons is less than about 0.1 weight % Thus, there is no significant alkylation of these lower aromatic hydrocarbons by the $C_9+$ aromatic compound, i.e., no significant transalkylation occurs as a side-reaction in the process of this invention. To demonstrate the process of the invention, a trimethyl benzene such as 1,2,4-trimethylbenzene was used.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid containing a $C_9+$ aromatic co pound, in the presence or absence of a hydrogen-containing fluid, with a catalyst composition can be carried out in any technically suitable manner, in batch, semicontinuous, or continuous process under a condition effective to convert a $C_9+$ aromatic compound to a $C_6$ to $C_8$ aromatic hydrocarbon. Generally, a fluid containing a $C_9+$ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9+$ aromatic compound fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3$ $H_2/ft^3$ catalyst/hour. The preferred molar ratio of $H_2$ to the $C_9+$ aromatic compound can be in the range of from about 0.01:1 to about 20:1, preferably about 0.1:1 to about 10:1, and most preferably 0.5:1 to 5:1. Generally, the pressure can be in the range of from about 30 to about 1000 psig, preferably about 50 to about 750 psig, and most preferably 200 to 600 psig, and the temperature is about 250 to about 1,000° C., preferably about 350 to about 800° C., and most preferably 400+ C to 650+ C.

The process effluent generally contains a heavies fraction of unconverted $C_9+$ aromatics and other heavy ($C_9+$) aromatic compounds which may have been formed by side-reactions (such as isomerization); a lights fraction of alkanes, mainly methane, ethane, propane, n-butane, isobutane, and minor amounts (about 0.1 to about 5 weight %) of $C_5$ and $C_6$ alkanes such as, for example, isopentane and n-pentane; and a BTX aromatic hydrocarbons fraction (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor described above, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400 to about 650° C., followed by a treatment with a reducing agent such as, for example, with hydrogen gas at a temperature of about 400 to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

According to the fourth embodiment of the invention, a process which can be used to prepare a catalyst composition is provided. The process can comprise, consist essentially of, or consist of, contacting an alumina-containing catalyst with a steam under a condition that is sufficient to effect the improvement of the catalyst activity or selectivity to a desired catalytic product. The alumina-containing catalyst can be an alumina, or alumina having incorporated therein or impregnated thereon a modifier, a promoter, or both. The presently preferred catalyst is a metal oxide-promoted alumina having incorporated therein an acid site modifier. The metal oxide can be the same as that disclosed above in the previous embodiments of the invention. The modifier can be any modifier so long as it improves the catalyst activity or selectivity to a desired product. The presently preferred modifier is the same as that disclosed above in the previous embodiments of the invention.

The steam treatment of an alumina-containing catalyst can be carried out under a condition sufficient to effect the production of a catalyst that has the characteristics described immediately above. Generally, the condition can include a temperature in the range of from about 120° C. to 1500° C., preferably about 200° C. to about 1200° C., and most preferably 250° C. to 1000° C.; a contacting period in the range of from about 5 minutes to about 30 hours, preferably about 20 minutes to about 25 hours, and most preferably 1 hour to 20 hours; a pressure in the range of from about 1 atmosphere to about 2,000 psig, preferably to about 1,500 psig, and most preferably to 1,000 psig.

The following examples are presented to further illustrate this invention and are not to be construed as unduly limiting the scope of the present invention. All impregnations were carried out by conventional incipient wetness method which is well known to one skilled in the art. The examples illustrate the preparation of catalyst compositions of the invention and the use of the composition in a hydrodealkylation process.

A γ-alumina obtained as 1/16 inch extrudates from Criterion Catalyst Company L.P., Michigan City, Ind. was used. First, an ammonium heptamolybdate solution was prepared by dissolving $(NH_4)_6Mo_7O_{24} \cdot 4H_2O$ in concentrated $H_3PO_4$ and water so that the ammonium molybdate concentration was 9.855 weight %, the $H_3PO_4$ concentration was 12.681 weight %, and water made up the rest. Then, 10 g of the alumina was impregnated at 25° C. with 5.32 g of the ammonium heptamolybdate solution to form a mixture. The mixture was then calcined in air at 538° C. for 6 hours to produce 10.18 g of a molybdenum oxide- and phosphorus oxide-impregnated alumina containing 2.807 weight % molybdenum and 2.096 weight % phosphorus (control catalyst).

Secondly, 15.32 g of the γ-alumina was impregnated with Mo and P by mixing with 7.96 g of the ammonium heptamolybdenum solution. The resulting mixture was, however, dried in air at 25° C. for 10 minutes followed by treating the resulting mixture in a U-tube with a steam at 650° C. for 6 hours to produce 15.51 g of a calcined molybdenum oxide- and phosphorus oxide-promoted alumina or $Mo-P/Al_2O_3$ containing 2.748 weight % of molybdenum and 2.059 phosphorus by calculation (invention catalyst A).

Thirdly, 42.21 g of a γ-alumina was impregnated with 20 g of a 50 weight % poly(phenylmethylsiloxane) (PPMS) in cyclohexane followed by calcining at 538° C. for 6 hours in air to produce 48.25 g of silicon oxide-modified alumina. Eight grams of the silicon oxide-modified alumina was then treated with 3.85 grams of the ammonium molybdate solution described above and then steamed as described above to produce a silicon oxide-, molybdenum oxide-, and phosphorus oxide-promoted alumina, $Si-Mo-P/Al_2O_3$, containing 2.409 weight % of molybdenum, 1.804 weight % phosphorus, and 12.518 weight % silicon oxide by calculation (invention catalyst B).

Fourthly, 10 g of a γ-alumina was impregnated with 4.85 g of a 10 weight % PPMS solution disclosed above followed by incorporated calcining at 538° C. for 6 hours to produce 10.37 g of $Si/Al_2O_3$ (silicon oxide-alumina). A similar batch of $Si/Al_2O_3$ was produced. Thereafter, 10.64 g of the pooled $Si/Al_2O_3$ was impregnated with 5.99 g of the ammonium heptamolybdate solution described above in a jar at 25° C. followed by air drying at 25° C. to no apparent excess moisture and then treating the resulting mixture in a U-tube with a steam at 650° C. for 6 hours to produce 11.28 g of a molybdenum oxide-, silicon oxide-, and phosphorus oxide-incorporated alumina containing 2.844 weight % molybdenum, 3.568 weight % $SiO_2$, and 2.130 weight % phosphorus by calculation (invention catalyst C).

In a separate run, 10 g of an γ-alumina was impregnated with 5.21 g of a 25 weight % PPMS solution as described above followed by calcining in air at 538° C. for 6 hours to produce 10.88 g of silicon oxide-modified alumina. A portion (7.56 g) of the silicon oxide-modified alumina was treated with 3.87 grams of the ammonium heptamolybdate solution described above to form a mixture. The mixture was allowed to stand for 10 minutes at 25° C. Thereafter, the mixture in a U-tube was heated with a steam at 650° C. for 6 hours to produce 7.94 g of phosphorus oxide-, silicon oxide-, and molybdenum oxide-promoted alumina (invention catalyst D). Catalyst D contained 8.088 weight % silicon oxide, 2.610 weight % molybdenum and 1.955 weight % of phosphorus by calculation.

These molybdenum oxide-promoted aluminas were then employed, according to the third embodiment of the invention, in a hydrodealkylation process for converting a $C_9+$ aromatic compound to BTX. The liquid feed in the hydrodealkylation runs was heavy $C_9+$ aromatic compounds obtained in a gasoline aromatization process in which gasoline was converted into BTX and $C_9+$ aromatic compounds. The composition of the feed is given in Table I which contained less than 800 ppm S by weight. Not given in Table I are numerous components which were in very small quantities and, in some instances, whose chemical structures were unknown.

TABLE I

Composition of Feed

| Feed Component | Weight Percent |
| --- | --- |
| c-Hexene-2 | 1.104 |
| 1-Methyl-3-ethylbenzene | 2.254 |
| 1-Methyl-4-ethylbenzene | 1.057 |
| 1, 3, 5-Trimethylbenzene | 1.958 |

TABLE I-continued

Composition of Feed

| Feed Component | Weight Percent |
| --- | --- |
| 1-Methyl-2-ethylbenzene | 1.306 |
| 1, 2, 4-Trimethylbenzene | 9.977 |
| 1, 2, 3-Trimethylbenzene | 3.060 |
| 1-Methyl-3-i-propylbenzene | 0.286 |
| 2, 3-Dihydroindene | 2.845 |
| 1, 3-Diethylbenzene | 1.173 |
| 1-Methyl-3-n-propylbenzene | 1.543 |
| 1, 4-Diethylbenzeneylbenzene | 0.910 |
| 1-Methyl-4-n-propylbenzene | 0.328 |
| n-Butylbenzene-ethylbenzene | 2.836 |
| 1-Methyl-2-n-propylbenzene | 0.889 |
| 1, 4,-Dimethyl-2-ethylbenzene | 1.991 |
| s-C5-benzene/1, 3-dimethyl-4-ethylbenzene | 2.958 |
| 1, 2-Dimethyl-4-ethylbenzene | 3.454 |
| 1, 2-Dimethyl-3-ethylbenzene | 1.007 |
| 1, 2, 4, 5-Tetramethylbenzene | 1.936 |
| 1, 2, 3, 5-Tetramethylbenzene | 2.695 |
| 5-Methylindan | 3.004 |
| 1-Ethyl-2-n-propylbenzene | 1.592 |
| 2-Methylindan | 3.040 |
| 1, 3-Di-i-propylbenzene | 1.084 |
| Naphthalene | 4.767 |
| 2-Methylnaphthalene | 3.382 |
| 1-Methylnaphthalene | 1.184 |

A stainless-steel reactor tube (inner diameter 0.75 inch; length 20 inches) was filled with a 20 ml bottom layer of Alundum® alumina (inert, low surface area alumina), one of the catalysts (in 1/16 inch extrudates) in the center position 5 ml, and a 20 ml top layer of Alundum® alumina. The catalysts were pretreated with hydrogen (260 ml/minute) at 575° C. (starting at 25° C. then ramping at 10° C./min) for one hour. The feed was then introduced into the reactor at a rate of 20 milliliters/hour (WHSV=about 4.5 to 4.9), together with hydrogen gas at a rate of 260 ml of $H_2$/hours. The reaction temperature was 573° C. to 579° C. as shown in Table II, and the reaction pressure was 500 psig. The reactor effluent was cooled and analyzed with an on-line gas chromatograph at intervals of about 1 hour. The results are shown in Table II.

modified with a silicon oxide, though have much higher catalyst activity (conversion) and selectivity to BTX than the control catalyst which was calcined, the rate of coke production was either suppressed or not significantly increased. The results for catalyst B showed little or no improvement over the control catalyst indicating that 12.518 weight % silicon oxide was probably detrimental to the catalyst.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A catalyst composition comprising a metal oxide-promoted alumina and phosphorus oxide, wherein the metal of said metal oxide is molybdenum.

2. A catalyst composition according to claim 1 wherein the weight ratio of said phosphorus oxide to said metal oxide-promoted alumina is in the range of from about 0.0001:1 to about 1:1.

3. A catalyst composition according to claim 1, wherein the weight ratio of said phosphorus oxide to said metal oxide-promoted alumina is in the range of from 0.005:1 to 0.5:1.

4. A catalyst composition according to claim 1 wherein the weight percent of said metal oxide in said catalyst composition is in the range of from 1 to 40%.

5. A catalyst composition comprising a metal oxide-promoted alumina, an acid site modifier, and phosphorus oxide, wherein the metal of said metal oxide comprises molybdenum, wherein said acid site modifier is a silicon oxide, wherein the weight ratio of said silicon oxide to said metal oxide-promoted alumina is in the range of from about 0.0001:1 to 0.11:1.

6. A catalyst composition according to claim 5 wherein the weight ratio of said silicon oxide to said metal oxide-promoted alumina is in the range of from 0.005:1 to 0.11:1.

7. A catalyst composition consisting essentially of an alumina, a metal oxide, a silicon oxide, and a phosphorus oxide wherein the metal of said metal oxide is molybdenum; the weight percent of said silicon oxide in said composition is in the range of from 0.5 to 33%; the weight percent of said phosphorus oxide in said composition is in the range of from 0.5 to 33%; and the weight percent of said metal oxide in said composition is in the range of from about 0.1 to about 60%.

TABLE II

| Catalyst | Catalyst Weight (g) | Reaction Time (° C.) | Reaction Time (hr) | Reactor Effluent (wt %)[a] | | | | |
| --- | --- | --- | --- | --- | --- | --- | --- | --- |
| | | | | Lights | BTX | Xyl | Conversion %[b] | Coke |
| Control | 3.37 | 576 | 7.25 | 9.3 | 22.2 | 15.2 | 34.2 | 3.8 |
| Invention A | 3.72 | 579 | 7.40 | 13.2 | 42.9 | 22.7 | 60.0 | 3.6 |
| Invention B | 3.85 | 578 | 7.32 | 9.9 | 21.2 | 14.1 | 33.6 | 3.2 |
| Invention C | 3.86 | 578 | 7.47 | 7.7 | 62.7 | 15.1 | 72.0 | 5.8 |
| Invention D | 3.55 | 574 | 7.57 | 11.5 | 58.6 | 21.8 | 72.7 | 4.1 |

[a]The values presented, except conversion, are weight percent. Xyl denotes the total weight % of all xylenes. The lights fraction included hydrocarbons shown in the text. The coke was determined at the end of each run by removing the catalyst from the reactor and determined with a thermal gravimetric analyzer (TGA), manufactured by TA Instruments, New Castle, Delaware. The values shown for coke are g/coke/hour.
[b]The % conversion was calculated as 100% - weight % unconverted $C_9$+ aromatic compounds in the reactor effluent.

The results shown in Table II indicate that the invention catalysts A, C, and D, which were produced by impregnation of alumina simultaneously with both ammonium heptamolybdate and phosphoric acid followed by steam treatment, significantly improved the yield of BTX and xylenes as well as the $C_9$+ conversion. Table II further demonstrates that steam treatment of molybdenum oxide-promoted catalyst 8. A catalyst composition made by a process comprising:
(1) contacting an alumina with an acid site modifier precursor under a condition sufficient to incorporate said acid site modifier precursor into said alumina to form an acid site-modified alumina;
(2) contacting said acid site-modified alumina with a phosphorus-containing compound and a metal compound under a condition sufficient to incorporate said phosphorus-containing compound and metal compound into said acid site-modified alumina to produce a modified alumina, wherein the metal of said metal compound is molybdenum; and
(3) steam-treating said modified alumina under a condition sufficient to effect the conversion of said metal compound to its corresponding metal oxide wherein said acid site modifier precursor is a silicon-containing compound.

9. A catalyst composition according to claim 8 wherein said silicon-containing compound is selected from the group consisting of poly(phenylmethylsiloxane), poly(phenylethylsiloxane), poly(phenylproplsiloxane), hexamethyldisiloxane, decamethyltetrasiloxane, diphenyltetramethyldisiloxane, tetraethyl orthosilicate, tetrabutyl orthosilicate, tetrapropyl orthosilicate, trimethylchlorosilane, chloromethyldimethylchlorosilane, N-trimethylsilylimidazole, N,O-bis(trimethylsilyl) acetamide, N-methyl-N-trimethylsilyltrifluoroacetamide, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl)aminopropyl]trimethoxysilane, cyanoethyltrimethoxysilane, aminopropyltriethoxysilane, phenyltrimethoxysilane, (3-chloropropyl)trimethoxysilane, (3-mercaptopropyl)trimethoxysilane, (3-glycidoxypropyl)trimethoxysilane, vinyltris($\beta$-methoxyethoxy)silane, ($\gamma$-methacryloxypropyl)trimethoxysilane, vinylbenzyl cationic silane, (4-aminoproyl)triethoxysilane, [$\gamma$-($\beta$-aminoethylamino)propyl]trimethoxysilane, ($\gamma$-glycidoxypropyl)trimethoxysilane, [$\beta$-(3,4-epoxycyclohexyl)ethyl]trimethoxysilane, ($\beta$-mercaptoethyl)trimethoxysilane, ($\gamma$-chloropropyl)trimethoxysilane, and combinations of any two or more thereof.

10. A catalyst composition according to claim 9 wherein said phosphorus-containing compound is selected from the group consisting of phosphorus pentoxide, phosphorus oxychloride, phosphoric acid, P(OR)$_3$, P(O)(OR)$_3$, P(O)(R)(R)(R), P(R)(R)(R), and combinations of any two or more thereof wherein R has one to about 10 carbon atoms and is independently selected from the group consisting of an alkyl radical, an alkenyl radical, an aryl radical, an aralkyl radical, an alkaryl radical, and combinations of any two or more thereof.

11. A catalyst composition according to claim 10 wherein said metal compound is ammonium heptamolybdate.

12. A catalyst composition according to claim 11 wherein said acid site modifier precursor is poly(phenylmethylsiloxane).

13. A catalyst composition according to claim 12 wherein said phosphorus-containing compound is phosphoric acid.

14. A catalyst composition according to claim 11 wherein said phosphorus-containing compound is phosphoric acid.

15. A catalyst composition according to claim 8 wherein said phosphorus-containing compound is selected from the group consisting of phosphorus pentoxide, phosphorus oxychloride, phosphoric acid, P(OR)$_3$, P(O)(OR)$_3$, P(O)(R)(R)(R), P(R)(R)(R), and combinations of any two or more thereof wherein R has one to about 10 carbon atoms and is independently selected from the group consisting of an alkyl radical, an alkenyl radical, an aryl radical, an aralkyl radical, an alkaryl radical, and combinations of any two or more thereof.

16. A catalyst composition made by a process comprising the steps of:
(1) contacting an alumina with an acid site modifier precursor under a condition sufficient to incorporate said acid site modifier precursor into said alumina to form an acid site-modified alumina;
(2) contacting said acid site-modified alumina with a phosphorus-containing compound and a metal compound under a condition sufficient to incorporate said phosphorus-containing compound and metal compound into said acid site-modified alumina to produce a modified alumina and
(3) treating said modified alumina with steam under a condition sufficient to effect the conversion of said metal compound to its corresponding metal oxide wherein said acid site modifier precursor is a silicon-containing compound and the metal of said metal compound is molybdenum.

17. A catalyst composition according to claim 16 wherein said silicon-containing compound is selected from the group consisting of poly(phenylmethylsiloxane), poly(phenylethylsiloxane), poly(phenylpropylsiloxane), hexamethyldisiloxane, decamethyltetrasiloxane, diphenyltetramethyldisiloxane, tetraethyl orthosilicate, tetrabutyl orthosilicate, tetrapropyl orthosilicate, trimethylehlorosilane, chloromethyldimethylchlorosilane, N-trimethylsilylimidazole, N,O-bis(trimethylsilyl) acetamide, N-methyl-N-trimethylsilyltrifluoroacetamide, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl)aminopropyl]trimethoxysilane, cyanoethyltrimethoxysilane, aminopropyltriethoxysilane, phenyltrimethoxysilane, (3-chloropropyl)trimethoxysilane, (3-mercaptopropyl)trimethoxysilane, (3-glycidoxypropyl)trimethoxysilane, , vinyltris($\beta$-methoxyethoxy)silane, ($\gamma$-methacryloxypropyl)trimethoxysilane, vinylbenzyl cationic silane, (4-aminoproyl)triethoxysilane, [$\gamma$-($\beta$-aminoethylamino)propyl]trimethoxysilane, [$\gamma$-glycidoxypropyl)trimethoxy silane, [$\beta$-(3,4-epoxycyclohexyl)ethyl]trimethoxysilane, ($\beta$-mercaptoethyl)trimethoxy silane, ($\gamma$-chloropropyl)trimethoxysilane, and combinations of any two or more thereof; and
said phosphorus-containing compound is selected from the group consisting of phosphorus pentoxide, phosphorus oxychloride, phosphoric acid, P(OR)$_3$, P(O)(OR)$_3$, P(O)(R)(R)(R), P(R)(R)(R), and combinations of any two or more thereof wherein R has one to about 10 carbon atoms and is independently selected from the group consisting of an alkyl radical, an alkenyl radical, an aryl radical, an aralkyl radical, an alkaryl radical, and combinations of any two or more thereof.

18. A catalyst composition according to claim 16 wherein said metal compound is ammonium heptamolybdate; said acid site modifier precursor is poly(phenylmethylsiloxane); and said phosphorus-containing compound is phosphoric acid.

19. A catalyst composition made by a process comprising (1) contacting a silicon-containing compound with an alumina to produce a silicon-modified alumina; (2) contacting said silicon-modified alumina with a phosphorus-containing compound and a molybdenum-containing compound to produce a modified alumina; and (3) steam-treating said modified alumina.

20. A catalyst composition according to claim 19 wherein said molybdenum-containing compound is ammonium heptamolybdate; said phosphorus-containing is phosphoric acid; and said silicon-containing compound is polyphenylmethylsiloxane.

* * * * *